(12) United States Patent
Venkata Narasayya et al.

(10) Patent No.: US 11,084,791 B2
(45) Date of Patent: Aug. 10, 2021

(54) SOLID STATE FORMS OF LENVATINIB MESYLATE

(71) Applicant: DR. REDDY'S LABORATORIES LIMITED, Hyderabad (IN)

(72) Inventors: Saladi Venkata Narasayya, Hyderabad (IN); Vamsi Krishna Mudapaka, Kothagudem (IN); Vishweshwar Peddy, Hyderabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 238 days.

(21) Appl. No.: 16/473,101

(22) PCT Filed: Dec. 29, 2017

(86) PCT No.: PCT/IB2017/058495
§ 371 (c)(1),
(2) Date: Jun. 24, 2019

(87) PCT Pub. No.: WO2018/122780
PCT Pub. Date: Jul. 5, 2018

(65) Prior Publication Data
US 2019/0345110 A1 Nov. 14, 2019

(30) Foreign Application Priority Data
Dec. 29, 2016 (IN) .............................. 201641044843

(51) Int. Cl.
*C07D 215/48* (2006.01)

(52) U.S. Cl.
CPC ........ *C07D 215/48* (2013.01); *C07B 2200/13* (2013.01)

(58) Field of Classification Search
CPC .......................... C07D 215/48; C07B 2200/13
See application file for complete search history.

(56) References Cited

U.S. PATENT DOCUMENTS

| 7,253,286 B2 | 8/2007 | Funahashi et al. |
| 7,612,208 B2 | 11/2009 | Matsushima et al. |
| 9,006,256 B2 | 4/2015 | Matsui |
| 10,246,418 B2 * | 4/2019 | Chen ..................... A61K 31/47 |

FOREIGN PATENT DOCUMENTS

| WO | 2016/155560 A1 | 10/2016 |
| WO | 2016/184436 A1 | 11/2016 |

OTHER PUBLICATIONS

International Search Report dated Mar. 23, 2018, for corresponding International Patent Application No. PCT/IB2017/058495.
Written Opinion dated Mar. 23, 2018, for corresponding International Patent Application No. PCT/IB2017/058495.
International Preliminary Report on Patentability dated Jul. 2, 2019, for corresponding International Patent Application No. PCT/IB2017/058495.

* cited by examiner

*Primary Examiner* — Timothy R Rozof
(74) *Attorney, Agent, or Firm* — Pergament & Cepeda LLP; Milagros A. Cepeda; Edward D. Pergament

(57) ABSTRACT

The present invention provides a crystalline form of Lenvatinib Mesylate, processes for the preparation of crystalline form of lenvatinib Mesylate and pharmaceutical compositions thereof. The crystalline form of lenvatinib Mesylate designated as Form VN1 is characterized by powder X-ray diffraction pattern. The present invention further provides a process for the preparation of amorphous form of lenvatinib Mesylate. The amorphous form is characterized by powder X-ray diffraction pattern.

11 Claims, 1 Drawing Sheet

SOLID STATE FORMS OF LENVATINIB MESYLATE

This application is a National Stage Application under 35 U.S.C. § 371 of PCT International Application No. PCT/IB2017/058495, filed Dec. 29, 2017, which takes priority from Indian Provisional Application Number IN 201641044843, filed Dec. 29, 2016, all of which is herein incorporated in its entirety.

INTRODUCTION

The present invention provides crystalline form of Lenvatinib Mesylate and process for its preparation. Also, the invention provides process for the preparation of amorphous form of Lenvatinib Mesylate.

BACKGROUND OF THE INVENTION

Lenvatinib Mesylate, 4-[3-chloro-4-(N'-cyclopropylureido)phenoxy]-7-methoxyquinoline-6-carboxamide methanesulfonate has the following chemical formula.

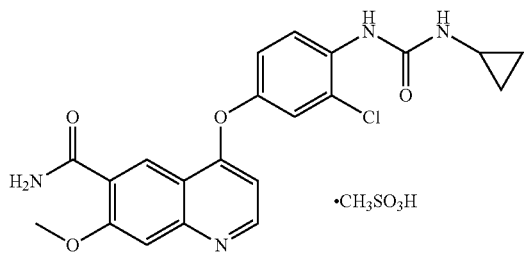

Lenvatinib Mesylate is a receptor tyrosine kinase (RTK) inhibitor that selectively inhibits the kinase activities of vascular endothelial growth factor (VEGF) receptors VEGFR1, VEGFR2, and VEGFR3. It is marked in the United States under the trade name LENVIMA® by Eisai, Inc. LENVIMA® is approved by the FDA for the treatment of patients with locally recurrent or metastatic, progressive, radioactive iodine-refractory differentiated thyroid cancer.

U.S. Pat. No. 7,253,286 describes Lenvatinib or pharmaceutically acceptable salts thereof. U.S. Pat. No. 7,612,208 describes crystalline forms Form A, B, C, F and I of Lenvatinib Mesylate and processes for their preparation.

WO 2016/184436 A1 describes Crystalline Form M of Lenvatinib Mesylate and process for its preparation. WO '436 discloses the use of acetonitrile for the crystallization of Lenvatinib Mesylate Form M.

The existence and possible numbers of polymorphic forms for a given compound cannot be predicted, and there are no "standard" procedures that can be used to prepare polymorphic forms of a substance. This is well-known in the art, as reported, for example, by A. Goho, "Tricky Business," Science News, Vol. 166(8), August 2004.

The discovery of new solid state forms and solvates of a pharmaceutical product may yield materials having desirable processing properties, such as storage stability, ease of handling, ease of processing, ease of purification, or may serve as desirable intermediate crystal forms that facilitate purification or conversion to other polymorphic forms. New solid state forms of a pharmaceutically useful compound can also provide an opportunity to improve the performance characteristics of a pharmaceutical product. Regulatory authorities require drug manufacturing companies to put efforts into identifying all polymorphic forms, e.g., crystalline, amorphous, solvates, stable dispersions with a pharmaceutically acceptable carriers, etc., of new drug substances. For at least these reasons, there is a need for additional solid state forms (including solvated forms) of Lenvatinib Mesylate.

The present invention provides a crystalline form of Lenvatinib Mesylate which is stable and has excellent physico-chemical properties. The crystalline form of Lenvatinib Mesylate of the present invention may be easily formulated into a pharmaceutical composition along with suitable pharmaceutically acceptable excipients.

SUMMARY OF THE INVENTION

In an aspect, the present invention provides a crystalline form of Lenvatinib Mesylate designated as Form VN1.

In another aspect, the present invention provides a crystalline form of Lenvatinib Mesylate designated as Form VN1, characterized by X-ray powder diffraction pattern having peaks at about 6.80, 15.92, 25.07, 26.41 and 29.04±0.20 degrees 2-theta and also having peaks at about 8.30, 10.70, 11.64, 19.26, 19.83, 20.86 and 21.51±0.20 degrees 2-theta.

In another aspect, the present invention provides crystalline form of Lenvatinib Mesylate designated as Form VN1, characterized by an X-ray powder diffraction pattern having peaks located substantially as illustrated in the pattern of FIG. 1.

In another aspect, the present invention provides a process for the preparation of crystalline form of Lenvatinib Mesylate Form VN1 comprising the steps of:
 a) combining lenvatinib with a suitable solvent or mixture thereof;
 b) mixing methane sulfonic acid with contents of step a);
 c) stirring the contents and isolating the product; and
 d) optionally, drying the product at suitable temperature.

In another aspect, the present invention provides a process for the preparation of crystalline form of Lenvatinib Mesylate Form VN1 comprising the steps of:
 a) combining Lenvatinib Mesylate with a suitable solvent or mixture thereof;
 b) optionally, filtering the un-dissolved particles;
 c) mixing the contents of step a) or step b) with a suitable anti-solvent;
 d) Isolating the product obtained; and
 e) optionally, drying the product at suitable temperature.

In another aspect, the present invention provides a process for the preparation of amorphous form of Lenvatinib Mesylate comprising the steps of:
 a) combining Lenvatinib Mesylate with a suitable solvent or mixture thereof;
 b) optionally filtering the un-dissolved particles;
 c) isolating the product from the filtrate of step b); and
 d) optionally, drying the product at suitable temperature.

DETAILED DESCRIPTION

In an aspect, the present invention provides a crystalline form of Lenvatinib Mesylate designated as Form VN1.

In an aspect, the crystalline form of Lenvatinib Mesylate designated as Form VN1 is Methyl Isobutyl Ketone (MIBK) solvate.

In another aspect, the present invention provides a crystalline form of Lenvatinib Mesylate designated as Form VN1, characterized by X-ray powder diffraction pattern having peaks at about 6.80, 15.92, 25.07, 26.41 and 29.04±0.20 degrees 2-theta and also having peaks at about 8.30, 10.70, 11.64, 19.26, 19.83, 20.86 and 21.51±0.20 degrees 2-theta.

Figure 1:
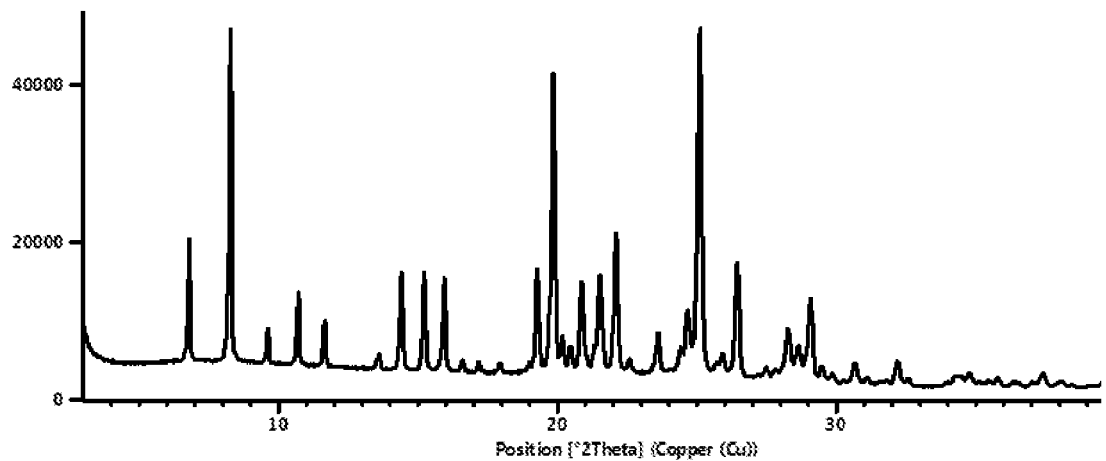
FIG. 1 shows an X-ray powder diffractogram of crystalline form of Lenvatinib Mesylate Form VN1.
Figure 2:
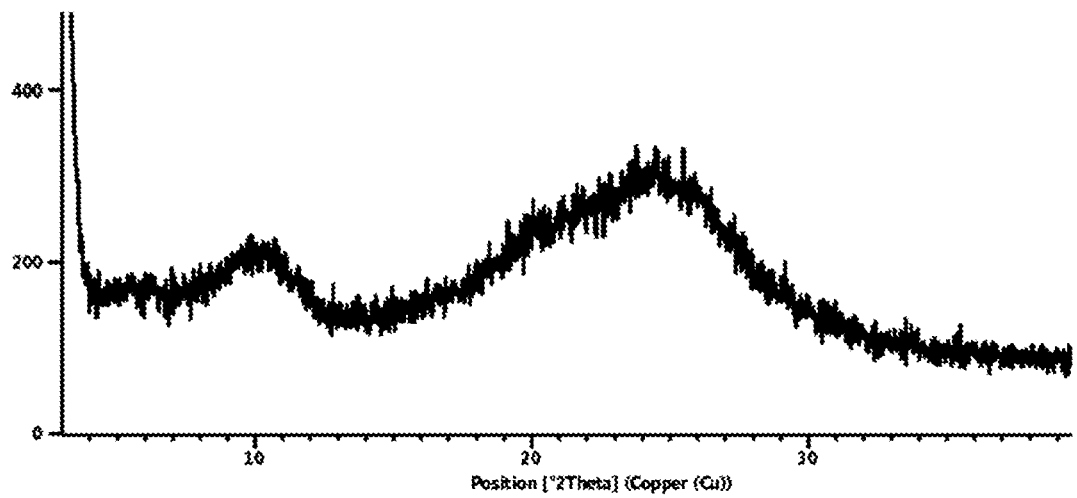
FIG. 2 shows an X-ray powder diffractogram of amorphous form of Lenvatinib Mesylate.

In another aspect, the present invention provides crystalline Lenvatinib Mesylate designated as Form VN1, characterized by an X-ray powder diffraction pattern having peaks located substantially as illustrated in the pattern of FIG. 1.

In an aspect, the methyl isobutyl ketone content in crystalline form of Lenvatinib Mesylate Form VN1 ranges from 10-20%.

In another aspect, the present invention provides a process for the preparation of crystalline form of Lenvatinib Mesylate Form VN1 comprising the steps of:
 a) combining Lenvatinib with a suitable solvent or mixture thereof;
 b) mixing methane sulfonic acid with contents of step a);
 c) stirring the contents and isolating the product; and
 d) optionally, drying the product at suitable temperature.

In step a) the suitable solvent or mixture of solvents used for combining with Lenvatinib include, but are not limited to ketones such as acetone, ethyl methyl ketone, 2-butanone, methyl isobutyl ketone. More specifically, the solvent is methyl isobutyl ketone.

Any particular form of Lenvatinib may be used as starting material for preparing Lenvatinib Mesylate Form VN1.

The step a) may be performed at a temperature of about 10° C. to about the boiling point of the solvent. In a preferred embodiment, the step a) is performed at 20-80° C. In a more preferred embodiment, the step a) is performed at 20-40° C.

In step b) the mixing of methane sulfonic acid with contents of step a) may be performed at performed at 20-80° C. In a more preferred embodiment, the step b) is performed at 20-40° C.

In step c), the contents are stirred at a temperature of about 10° C. to about the boiling point of the solvent. In a preferred embodiment, the step c) is performed at 20-80° C. In a more preferred embodiment, the step c) is performed at 20-40° C.

Isolation in step c) may involve one or more methods including removal of solvent by techniques known in the art e.g. evaporation, distillation, filtration of precipitated solid and the like, cooling, concentrating the reaction mass, and the like. Stirring or other alternate methods such as shaking, agitation, and the like, may also be employed for the isolation. Isolation may be performed at a temperature of about 20-60° C. More preferably, the isolation is at temperature of about 20-40° C.

Drying may be done using any equipment such as a gravity oven, tray dryer, vacuum oven, Rotavapor®, air tray dryer, fluidized bed dryer, spin flash dryer, flash dryer, and the like.

In an embodiment, the drying may be carried out at atmospheric pressure or under reduced pressure. In an embodiment, the drying may be carried out at a temperature of about 60° C., at a temperature of about 50° C., at a temperature of about 40° C. or at a temperature of about 30° C. The drying may be carried out for any time periods required for obtaining a desired quality, such as from about 15 minutes to several hours, or longer.

In another aspect, the present invention provides a process for the preparation of crystalline form of Lenvatinib Mesylate Form VN1 comprising the steps of:
 a) combining Lenvatinib Mesylate with a suitable solvent or mixture thereof;
 b) optionally, filtering the un-dissolved particles;
 c) mixing the contents of step a) or step b) with a suitable anti-solvent;
 d) isolating the product obtained; and
 e) optionally, drying the product at suitable temperature.

Any particular form of Lenvatinib Mesylate may be used as starting material for preparing Lenvatinib Mesylate Form VN1.

In step a) the suitable solvent or mixture of solvents used for combining with Lenvatinib Mesylate include, but are not limited to dimethylformamide; dimethylacetamide; N-Methyl-2-pyrrolidone; acids such as acetic acid, formic acid; alcohols such as methanol, ethanol, benzyl alcohol, propylene glycol; mixtures thereof. Specifically, the solvent is selected from methanol, ethanol, acetic acid, formic acid, N-Methyl-2-pyrrolidone and mixtures thereof. More specifically the solvent is acetic acid and methanol.

The step a) may be performed at a temperature of about 10° C. to about the boiling point of the solvent. In a preferred embodiment, the step a) is performed at 20-80° C. In a more preferred embodiment, the step a) is performed at 20-60° C.

Step c) involves mixing with a suitable anti-solvent. The anti-solvent used is methyl isobutyl ketone. In step c) the mixing of anti-solvent with contents of step a) or step b) may be performed at performed at about 20-80° C. In a more preferred embodiment, the step b) is performed at 20-60° C.

Isolation in step d) may involve one or more methods including removal of solvent by techniques known in the art e.g. evaporation, distillation, filtration of precipitated solid and the like, cooling, concentrating the reaction mass, and the like. Stirring or other alternate methods such as shaking, agitation, and the like, may also be employed for the isolation. Isolation may be performed at a temperature of about 20-60° C. More preferably, the isolation is at temperature of about 20-40° C.

Drying may be done using any equipment such as a gravity oven, tray dryer, vacuum oven, Rotavapor®, air tray dryer, fluidized bed dryer, spin flash dryer, flash dryer, and the like. In an embodiment, the drying may be carried out at atmospheric pressure or under reduced pressure. In an embodiment, the drying may be carried out at a temperature of about 60° C., at a temperature of about 50° C., at a temperature of about 40° C. or at a temperature of about 30° C. The drying may be carried out for any time periods required for obtaining a desired quality, such as from about 15 minutes to several hours, or longer.

In another aspect, the present invention provides a process for the preparation of amorphous form of Lenvatinib Mesylate comprising the steps of:
 a) combining Lenvatinib Mesylate with a suitable solvent or mixture thereof;
 b) optionally filtering the un-dissolved particles;
 c) isolating the product from the filtrate of step b); and
 d) optionally, drying the product at suitable temperature.

Any crystalline form of Lenvatinib Mesylate may be used as starting material for preparing amorphous Lenvatinib Mesylate.

In step a) the suitable solvent or mixture of solvents used for combining with Lenvatinib Mesylate include, but are not limited to dimethylformamide; dimethylacetamide; N-Methyl-2-pyrrolidone; acids such as acetic acid, formic acid; alcohols such as methanol, ethanol, benzyl alcohol, propylene glycol; mixtures thereof. Specifically, the solvent is selected methanol, ethanol, acetic acid, formic acid, N-Methyl-2-pyrrolidone and mixtures thereof.

The step a) may be performed at a temperature of about 10° C. to about the boiling point of the solvent.

Isolation of amorphous Lenvatinib Mesylate may involve one or more methods including removal of solvent by techniques known in the art e.g. solvent evaporation, distillation, filtration of precipitated solid, concentrating the reaction mass, and the like. Stirring or other alternate methods such as shaking, agitation, and the like, may also be employed for the isolation. One of the embodiments also relates to addition of an anti-solvent to the solution of step a) or step b) to precipitate amorphous Lenvatinib Mesylate. Distillation of the solvent may be conducted at atmospheric pressure or above, or under reduced pressures and at a temperatures less than about 120° C., less than about 100° C., less than about 90° C., or any other suitable temperatures. Any temperature and vacuum conditions can be used as long as there is no increase in the impurity levels of the product due to decomposition.

The resulting solid may be collected by using techniques such as by scraping or by shaking the container or other techniques specific to the equipment used. The isolated solid may be optionally further dried to afford pure amorphous form of Lenvatinib Mesylate.

Drying may be done using any equipment such as a gravity oven, tray dryer, vacuum oven, Rotavapor®, air tray dryer, fluidized bed dryer, spin flash dryer, flash dryer, and the like. In an embodiment, the drying may be carried out at atmospheric pressure or under reduced pressure. In an embodiment, the drying may be carried out at a temperature of about 60° C., at a temperature of about 50° C., at a temperature of about 40° C. or at a temperature of about 30° C. The drying may be carried out for any time periods required for obtaining a desired quality, such as from about 15 minutes to several hours, or longer.

In one embodiment, the present invention provides pharmaceutical composition comprising crystalline form of Lenvatinib Mesylate designated as Form VN1 and at least one pharmaceutically acceptable excipient.

Pharmaceutically acceptable excipients include, but are not limited to, suitable surface modifiers. Such excipients include various polymers, low molecular weight oligomers, natural products, and surfactants.

All PXRD data reported herein are obtained using a PANalytical X-ray Diffractometer, with copper Kα radiation.

Definitions

The following definitions are used in connection with the present application unless the context indicates otherwise.

The terms "about," the like are to be construed as modifying a term or value such that it is not an absolute. Such terms will be defined by the circumstances and the terms that they modify as those terms are understood by those of skill in the art. This includes, at very least, the degree of expected experimental error, technique error and instrument error for a given technique used to measure a value.

All percentages and ratios used herein are by weight of the total composition and all measurements made are at about 25° C. and about atmospheric pressure, unless otherwise designated. All temperatures are in degrees Celsius unless specified otherwise. As used herein, the terms "comprising" and "comprises" mean the elements recited, or their equivalents in structure or function, plus any other element or elements which are not recited. The terms "having" and "including" are also to be construed as open ended. All ranges recited herein include the endpoints, including those that recite a range between two values. Whether so indicated or not, all values recited herein are approximate as defined by the circumstances, including the degree of expected experimental error, technique error, and instrument error for a given technique used to measure a value.

The term "optional" or "optionally" is taken to mean that the event or circumstance described in the specification may or may not occur, and that the description includes instances where the event occurs and instances where it does not.

The term "anti-solvent" may be taken to mean a solvent in which lenvatinib or its salts have low solubility.

Certain specific aspects and embodiments of the present invention will be explained in more detail with reference to the following examples, which are provided only for purposes of illustration and should not be construed as limiting the scope of the present application in any manner.

EXAMPLES

Preparation of Lenvatinib Mesylate Form VN1

Example 1

Lenvatinib (0.5 g) and Methyl isobutyl ketone (10 mL) were taken in a vial at 25-30° C. and stirred. Methane sulfonic acid (0.24 g) was added to the above vial and stirred for 24 hours. The contents of the above vial were filtered to obtain title compound.

Result: Form VN1

Example 2

Lenvatinib Mesylate (2 g) and acetic acid (20 mL) were taken in a flask and heated to 50° C. The contents were filtered for any un-dissolved particle and the clear solution was transferred to an easy max reactor. To this, Methyl Isobutyl Ketone (60 mL) was added at 25° C. and stirred for 2-3 hours. The contents were filtered and dried in vacuum tray dryer at 35° C. for 12-14 hours to yield the title compound.

Result: Form VN1

Example 3

Lenvatinib Mesylate (1 g) and Methanol (100 mL) were taken in a flask and heated to 50° C. The contents were filtered for any un-dissolved particle and the clear solution was transferred to an easy max reactor. To this, Methyl Isobutyl Ketone (300 mL) was added at 25° C. and stirred for 14-15 hours. The contents were filtered and dried in vacuum tray dryer at 45° C. for 3-4 hours to yield the title compound.

Result: Form VN1

Example 4

Lenvatinib Mesylate (1.0 Kg) and acetic acid (10.0 L) were taken in a reactor at 25° C. and heated to 40° C. for 15-30 minutes. The contents were filtered for any un-dissolved particle and the clear solution was cooled to 30° C. Methyl Isobutyl Ketone (20.0 L) and Lenvatinib Mesylate MIBK solvate seed material (20 g) were added to the above reaction mass and stirred for 2-3 hours at 30° C. The reaction mass was filtered through Pressure Nutsche filter (PNF) by applying nitrogen and the wet material was washed with Methyl Isobutyl Ketone (3.0 L) at 30° C. The wet material was dried in vacuum tray drier (with vacuum not less than 650 mm Hg) at 42° C. for 16-20 hours to afford the title compound.

Result: Form VN1

Example 5

Lenvatinib Mesylate (95 g) and acetic acid (950 ml) were taken in a reactor at 25° C. and heated to 40° C. for 15-30 minutes. The contents were filtered for any un-dissolved particle and the clear solution was cooled to 30° C. Methyl Isobutyl Ketone (950 ml) was charged to the above flask and an additional amount of Methyl Isobutyl Ketone (1900 ml) was added over a period of 2 hours at 25-30° C. The reaction mass is stirred for 2-3 hours at 25-30° C. and filtered. The wet material was washed with Methyl Isobutyl Ketone (285 ml) at 25-30° C. The wet material was dried in vacuum tray drier (with vacuum not less than 650 mm Hg) at 40° C. for 12-14 hours to afford the title compound.

$^1$H NMR (600 MHz, DMSO-$d_6$) δ (ppm): 8.96-8.95 (d, 1H), 8.72 (s, 1H), 8.37-8.36 (d, 1H), 8.06 (s, 1H), 7.96 (s, 1H), 7.89 (s, 1H), 7.63-7.61 (m, 2H), 7.36-7.34 (m, 1H), 7.25 (d, 1H), 6.93-6.92 (d, 1H), 4.08 (s, 3H), 3.51 (bs, 1H), 2.60-2.57 (m, 1H), 2.38 (s, 3H), 2.32 (s, 3H), 2.29-2.28 (d, 2H), 2.05 (s, 2.5H), 2.03-1.97 (m, 1H), 0.85-0.84 (m, 5.7H), 0.68-0.67 (m, 2H), 0.44 (m, 2H).

$^{13}$C NMR (150 MHz, DMSO-d6) δ (ppm): 208.1, 166.9, 164.7, 160.9, 155.3, 148.3, 146.1, 143.1, 135.6, 128.0, 125.2, 122.0, 121.8, 121.7, 120.2, 114.1, 103.5, 101.1, 56.8, 51.7, 29.9, 23.8, 22.3, 22.2, 6.1.

Example 6

Lenvatinib Mesylate (1.0 Kg) and acetic acid (10.0 L) were taken in a reactor at 30° C. and heated to 45° C. for 15-30 minutes. The contents were filtered for any un-dissolved particle and the clear solution was cooled to 35° C. Methyl Isobutyl Ketone (30.0 L) was added to the above reaction mass and stirred for 2-3 hours at 30° C. The reaction mass was filtered through Pressure Nutsche filter (PNF) and the wet material was washed with Methyl Isobutyl Ketone (3.0 L) at 30° C. The wet material was dried in vacuum tray drier (with vacuum not less than 650 mm Hg) at 42° C. for 18-22 hours to afford the title compound.

Result: Form VN1

Example 7: Preparation of Amorphous Lenvatinib Mesylate

Lenvatinib Mesylate (5 g) and Methanol (500 mL) were taken in a flask and heated to 60° C. The contents were filtered for any un-dissolved particle and the clear solution was transferred to spray dryer flask. The filtrate was spray dried to obtain the title compound. The parameters for the spray drying equipment are: Inlet temperature 60° C., aspirator 70% and feed pump 20%.

Result: Amorphous Lenvatinib Mesylate.

The invention claimed is:

1. Methyl Isobutyl Ketone solvate of Lenvatinib Mesylate.

2. A Crystalline Methyl Isobutyl Ketone solvate of Lenvatinib Mesylate.

3. The Crystalline Methyl Isobutyl Ketone solvate of Lenvatinib Mesylate according to claim 2, having an X-ray diffraction pattern comprising peaks at about 6.80, 15.92, 25.07, 26.41 and 29.04±0.20 degrees 2-theta.

4. The Crystalline Methyl Isobutyl Ketone solvate of Lenvatinib Mesylate according to claim 3, having an X-ray diffraction pattern comprising further peaks at 8.30, 10.70, 11.64, 19.26, 19.83, 20.86 and 21.51±0.20 degrees 2-theta.

5. The Crystalline Methyl Isobutyl Ketone solvate of Lenvatinib Mesylate according to claim 2, having an X-ray diffraction pattern as shown in FIG. 1.

6. A process for preparing crystalline Methyl Isobutyl Ketone solvate of Lenvatinib Mesylate, comprising the steps of:
   a) mixing lenvatinib free base and Methyl Isobutyl Ketone;
   b) mixing either concentrated methane sulphonic acid or an organic solution of methane sulphonic acid with the mixture from step (a); and
   c) isolating the Methyl Isobutyl Ketone solvate of Lenvatinib Mesylate.

7. The process of claim 6, wherein the organic solvent is Methyl Isobutyl Ketone.

8. A process for preparing crystalline Methyl Isobutyl Ketone solvate of Lenvatinib Mesylate, comprising the steps of:
   a) mixing Lenvatinib Mesylate and a solvent or mixture of solvents;
   b) mixing Methyl Isobutyl Ketone with the mixture from step (a); and
   c) isolating the Methyl Isobutyl Ketone solvate of Lenvatinib Mesylate.

9. The process of claim 8, wherein the solvent or mixture of solvents is selected from dimethylformamide, dimethylacetamide, N-Methyl-2-pyrrolidone, acetic acid, methanol, ethanol or mixtures thereof.

10. The Crystalline Methyl Isobutyl Ketone solvate of Lenvatinib Mesylate according to claim 3, having an X-ray diffraction pattern as shown in FIG. 1.

11. The Crystalline Methyl Isobutyl Ketone solvate of Lenvatinib Mesylate according to claim 4, having an X-ray diffraction pattern as shown in FIG. 1.

* * * * *